(12) United States Patent
De Jong et al.

(10) Patent No.: US 10,487,125 B2
(45) Date of Patent: Nov. 26, 2019

(54) ICE STRUCTURING PROTEIN

(71) Applicant: DSM IP ASSETS B.V., Heerlen (NL)

(72) Inventors: René Marcel De Jong, Echt (NL); Petrus Jacobus Theodorus Dekker, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/039,110

(22) PCT Filed: Dec. 2, 2014

(86) PCT No.: PCT/EP2014/076291
§ 371 (c)(1),
(2) Date: May 25, 2016

(87) PCT Pub. No.: WO2015/082488
PCT Pub. Date: Jun. 11, 2015

(65) Prior Publication Data
US 2017/0029476 A1  Feb. 2, 2017

(30) Foreign Application Priority Data

Dec. 2, 2013 (EP) ..................... 13195351

(51) Int. Cl.
*C12N 15/81* (2006.01)
*C07K 14/39* (2006.01)
*A23G 9/38* (2006.01)

(52) U.S. Cl.
CPC ............. *C07K 14/39* (2013.01); *A23G 9/38* (2013.01); *C12N 15/81* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,118,792 A | 6/1992 | Warren et al. | |
| 6,914,043 B1 | 7/2005 | Chapman et al. | |
| 9,012,179 B2 | 4/2015 | Kim et al. | |
| 2008/0038286 A1* | 2/2008 | Geng | A61K 39/0002 424/188.1 |
| 2012/0107873 A1* | 5/2012 | Vind | A23C 9/1307 435/69.1 |
| 2014/0134300 A1* | 5/2014 | Bramley | A23G 9/38 426/91 |

FOREIGN PATENT DOCUMENTS

| | | |
|---|---|---|
| EP | 2602263 A2 | 6/2013 |
| KR | 20100137056 A | 12/2010 |
| KR | 10-2012-0126794 A | 11/2012 |
| WO | 90/13571 A1 | 11/1990 |

OTHER PUBLICATIONS

Lee et al in "Optimization of the pilot-scale production of an ice-binding protein by fed-batch culture of Pichia pastoris" (published online Dec. 1, 2012: Appl Microbiol Biotechnol (2013) vol. 97: pp. 3383-3393).*
Li et al., "Structure and function of an antifreeze polypeptide from ocean pout, Macrozoarces americanus: role of glutamic acid residues in protein stability and antifreeze activity by site-directed mutagenesis." Protein Engineering vol. 4 No. 8 pp. 1003-1008. 1991.
Smallwood et al., "Isolation and characterization of a novel antifreeze protein from carrot (*Daucus Carota*)." Biochem. J. (1999) 340, 385-391 (Printed in Great Britain).
Tomczak et al., "A facile method for determining ice recrystallization inhibition by antifreeze proteins." Biochemical and Biophysical Research Communications 311 (2003) 1041-1046.
Regulation (EC) No. 258/97 of the European Parliament and of the Council of Jan. 27, 1991, concerning novel foods and novel food ingredients, Official Journal of the European Communities.
Griffith, "Antifreeze Proteins and Their Potential Use in Frozen Foods." Biotechnology Advances, vol. 13, No. 3, pp. 375-402, 1995.
Lee et al., "Optimization of the pilot-scale production of an ice-binding protein by fed-batch culture of Pichia pastoris." Appl Microbiol Biotechnol (2013), Biotechnological Products and Process Engineering Received Appl Microbiol Biotechnol (2013) 97:3383-3393.
Steiner et al., "Sequence and promoter analysis of the highly expressed TEF gene of the filamentous fungus *Ashbya gossypii*." Mol Gen Genet (1994) 242: 263-271, XP-002127171.
Ribeiro et al., "Expression of Trichoderma reesei cellulases CBHI and EGI in Ashbya gossypii." Appl Microbiol Biotechnol (2010) 87:1437-1446, XP019841608.
Lee et al., "An extracellular ice-binding glycoprotein from an Arctic psychrophilic yeast." Cryobiology 60 (2010) 222-228, XP026933530.
Lee et al., Optimization of the pilot-scale production of an ice-binding protein by fed-batch culture of Pichia pastoris. Appl Microbiol Biotechnol (2013) 97: 3383-3393, XP055099913.
Jeenes et al., "Regulation of secreted protein production by filamentous fungi: recent developments and perspectives." Journal of General Microbiology (1993) 139: 2295-2307, XP055099938.
International Search Report dated May 11, 2015, issued in PCT/EP2014/076291.

* cited by examiner

*Primary Examiner* — Catherine S Hibbert
(74) *Attorney, Agent, or Firm* — McBee Moore Woodward & Vanik IP, LLC

(57) ABSTRACT

The present invention relates to a nucleic acid construct comprising: a nucleic acid sequence encoding an ice structuring protein (ISP) comprising the sequence set out in SEQ ID NO: 1 or a sequence at least 80% identical thereto or comprising the sequence set out in amino acids 21 to 261 of SEQ ID NO: 1 or a sequence at least 80% identical thereto; and, linked operably thereto, control sequences permitting expression of the nucleic acid sequence in a filamentous fungal host cell. The construct may be used in a method for the production of an ISP, wherein the ISP is expressed in a filamentous fungal host cell.

19 Claims, 5 Drawing Sheets

Specification includes a Sequence Listing.

ICE STRUCTURING PROTEIN

CROSS-REFERENCE TO RELATED APPLICATIONS

This application is a § 371 National Stage Application of PCT/EP2014/076291, filed 2 Dec. 2014, which claims priority to EP 13195351.5, filed 2 Dec. 2013.

FIELD OF THE INVENTION

The present invention relates to a nucleic acid construct comprising a nucleic acid sequence encoding an ice structuring protein (ISP). The invention also relates to an expression vector comprising the nucleic acid and to a filamentous fungal host cell which comprises the nucleic acid construct or the expression vector. The invention further relates to a method for the production of an ISP, to an ISP obtainable by such a method, to an ISP, to a food composition comprising such ISPs, to a method for the preparation of a food composition using the ISPs and to use of the ISPs in a food composition.

BACKGROUND TO THE INVENTION

An interesting group of proteins that has potentially many application possibilities is ice structuring proteins (ISP), often referred to as antifreeze proteins (AFP).

Warren et al. (U.S. Pat. No. 5,118,792) have suggested adding purified ISPs directly to food products prior to freezing to improve preservation characteristics during frozen storage. WO90/13571 A1 teaches methods of improving the freeze tolerance of food products by suppressing ice crystal growth or inhibiting ice recrystallization using antifreeze polypeptides in isolated form. A wide range of applications for ISP's in food and non-food have been suggested in the past, e.g. exemplified in Griffith and Vanya Ewart (1995) Biotechnology Advances 13:375-402 and EP2602263A2. However, many applications are currently economically not feasible due to the high cost in use of ISP.

Cost in use of such ISP's must be as low as possible to allow development of many different applications. Although the AFP type III HPLC12 from ocean pout is currently used for ice cream production on industrial scale, the difficulties associated with producing ISPs in large quantities at an economic attractive price preclude them from use in other industrial applications. An ideal ISP that can be used in different applications would be highly active at low concentration, low in cost, readily available, and simple to use.

A low cost in use of ISP can be obtained by selecting an ISP that has high ice structuring activity per mol protein. The minimal concentration of the best studied, and industrially used ISP (type III AFP from ocean pout) to obtain recrystallization inhibition in a 30% sucrose solution at −6° C. has been reported to be >700 nM (Smallwood et al (1999) Biochem. J. 340:385-391; Tomczak et al (2003) Biochem. BiophysRes. Comm. 311: 1041-1046). Consequently, a relatively high concentration of ISP is required in the application to obtain satisfactory results. Unilever has reported that the concentration of ISP (type III AFP) in ice cream application is ~50 mg/kg (w/w) (Lewis (2006) Application for the Approval of Ice Structuring Protein Type III HPLC 12 Preparation for use in Edible Ices, Regulation (EC) No 258/97 of the European Parliament and of the Council of 27th January 1997 Concerning Novel Foods and Novel Food Ingredients), which is equivalent to 7 µM for this ISP. It has also been reported that ice crystal growth can be inhibited by 3-25 µM type III AFP (Li and Hew (1991) Protein engineering 4:1003-1008). An ISP which gives a similar effect with a lower required dosage would be beneficial for decreasing the cost-in-use of these proteins and would open up the possibility to develop additional applications.

Also high expression of ISP per kg fermentation broth will lead to a reduced cost price and a low cost-in-use. High expression will also lead to a more pure product that only requires a minimum of purification, thus further reducing cost price.

The productivity of ISP's that are currently described in literature is however low. Expression of type III AFP from ocean pout in the bakers' yeast *Saccharomyces cerevisiae* has been reported to be difficult (U.S. Pat. No. 6,914,043 B1) and only detectable when the culture broth supernatant was undiluted, suggesting a low level of expression.

Also expression of the ISP of *Leucosporidium* (LeIBP) in *Escherichia coli* or *Pichia pastoris* is described to be between 2.1 and 61.2 mg per liter culture broth in shake flask (Park et al (2012) Cryobiology 64:286-296), despite the track record of both microorganisms to successfully express heterologous proteins at high level.

Recently Lee et al have summarized all literature on the expression of known ISP's and concluded that expression levels do not exceed 175 mg/l (Lee et al (2013) Appl. Microbiol. Biotechnol. 97:3383-3393). They suggest that the application of ISP's is largely hampered by the lack of an economic production systems.

The same authors managed to increase productivity of LeIBP to ~300 mg/l by a combined fed batch and induction of production by addition of methanol at reduced temperature. Due to the low productivity in fermentation, the protein had to be concentrated and purified before it could be used in further experiments, leading to a very poor yield and consequently a high cost price. Such measures may be useful for lab scale fermentation but are not economic for industrial production. Because of this the cost in use of the currently described ISP's is high and therefore the use of ISP in industry is limited.

Besides the cost in use it is also important that the end product has GRAS status (Generally Regarded As Safe) for the application of an ISP in a food product. Many of the ISPs described in literature are expressed in micro-organisms or produced with processes lacking this status and can therefore not be used in food applications. For example LeIBP is currently expressed in *Pichia pastoris*, a yeast which requires the addition of toxic methanol for induction of the expression of LeIBP (Lee et al (2013)).

Accordingly, there is a need for an ISP that is highly active, low in cost, readily available in food-grade form, and simple to use.

SUMMARY OF THE INVENTION

The present invention is based on the successful expression of the ice structuring protein from *Leucosporidium* sp. (AFP19) in a filamentous fungus. The expression level of AFP19 is, surprisingly, exceptionally high in filamentous fungi, much higher than described in literature for expression in bacteria or yeast.

Moreover, AFP19 as expressed in filamentous fungi shows very good ice re-crystallization inhibition activity at extremely low concentrations. This ISP is shown to be active in ice recrystallization at ~20 nM, a 35-fold lower concentration than found for the current industry standard type III AFP from ocean pout.

Surprisingly, productivity of AFP19 in a filamentous fungus was higher than 1 g/l at shake flask scale. Productivity of the same protein at shake flask scale in yeast or bacteria has been reported in literature to be a factor 15-500 lower (named LeIBP). Therefore the cost in use of AFP19 expressed in filamentous fungi will be much lower than all currently known ISP's. Consequently many more industrial applications may be economically possible using AFP19 expressed in filamentous fungi as compared with currently known ISPs.

Furthermore, it appears that the ISP as produced in a filamentous fungus is a stable protein: possible stabilizing properties are N- or O-glycosylation and/or a block by pyroglutamate at the N-terminus According to the invention, there is thus provided A nucleic acid construct comprising:

a nucleic acid sequence encoding an ice structuring protein (ISP) comprising the sequence set out in SEQ ID NO: 1 or a sequence at least 80% identical thereto or comprising the sequence set out in amino acids 21 to 261 of SEQ ID NO: 1 or a sequence at least 80% identical thereto; and, linked operably thereto, control sequences permitting expression of the nucleic acid sequence in a filamentous fungal host cell.

The invention also provides:

an expression vector comprising a nucleic acid construct of the invention;

a filamentous fungal host cell which comprises a nucleic acid construct or an expression vector of the invention;

a method for the production of an ice structuring protein (ISP), which method comprises:

providing a filamentous fungal host cell which comprises a nucleic acid sequence encoding an ISP comprising the sequence set out in SEQ ID NO: 1 or a sequence at least 80% identical thereto or comprising the sequence set out in amino acids 21 to 261 of SEQ ID NO: 1 or a sequence at least 80% identical thereto, wherein the said nucleic acid sequence is operably linked to control sequences permitting expression of the nucleic acid sequence in the filamentous fungal host cell;

cultivating the filamentous fungal host cell under conditions suitable for production of the ice structuring protein; and, optionally recovering the ice structuring protein;

an ice structuring protein obtainable by a method of the invention;

an ice structuring protein comprising the sequence set out in SEQ ID NO: 1 or a sequence at least 80% identical thereto or comprising the sequence set out in amino acids 21 to 261 of SEQ ID NO: 1 or a sequence at least 80% identical thereto, wherein:

at least one amino acid is a modified amino acid;

at least one amino acid is O-mannosylated; or the protein has a glycosylation pattern other than 2GlcNac and 2 hexose units;

a food composition comprising an ice structuring protein of the invention;

a method for the preparation of a food composition, which method comprises combining an ice structuring protein according of the invention with one or more food ingredients;

use of an ice structuring protein of the invention in a food composition; and a food composition or use of the invention, wherein the food composition is a frozen confectionary product, such as an ice cream or a sorbet.

DESCRIPTION OF THE SEQUENCE LISTING

Figure 1:
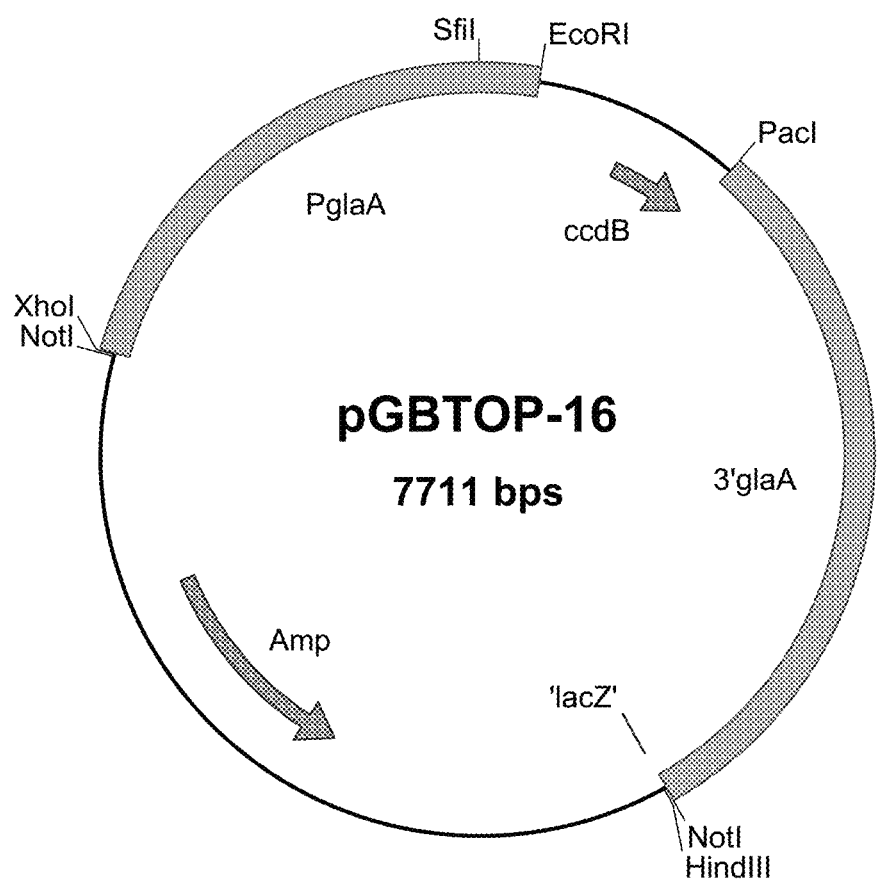
FIG. 1 shows a physical map of the pGBTOP-16 vector used for cloning of the AFP19 gene. The pGBTOP-16 vector is derived from the pGBTOP-12 vector described in WO2011/009700. In addition to pGBTOP-12, it contains the ccdB gene from *E. coli* for positive selection for presence of an insert between the EcoRI and PacI cloning sites. The PacI restriction site replaces the SnaBI restriction site present in pGBTOP-12.

SEQ ID NO: 1 sets out the protein sequence of the ISP of *Leucosporidium* (AFP19). This sequence consists of a signal sequence of 20 amino acids for efficient secretion in *Leucosporidium* and a deduced mature protein sequence of 241 amino acids. The amino acid sequence of AFP19 of *Leucosporidium* is also set out in Swiss-Prot/TrEMBL (accession number: C7F6X3) and Genbank accession number ACU30807.1.

SEQ ID NO: 2 sets out a codon-adapted DNA sequence for expression of SEQ ID NO: 1 in *Aspergillus niger*

SEQ ID NO: 3 sets out a codon-adapted DNA sequence for expression of SEQ ID NO: 1 in *Aspergillus niger* containing additional restriction sites for subcloning in an *Aspergillus* expression vector.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The present invention relates to the expression of an ice structuring protein (ISP), for example that from a *Leucosporidium* sp., such as AFP19, the full length amino acid sequence of which is set out in SEQ ID NO: 1, in a filamentous fungus. The expression level of such proteins has been demonstrated to be unexpectedly and exceptionally high in filamentous fungi; much higher than expression levels described in literature for bacteria or yeast.

In addition, the ISP of the invention, as expressed using filamentous fungus, can be distinguished, at the chemical level, from the equivalent protein isolated either from a wild-type source or from an equivalent protein as expressed in bacteria or yeast.

The ISP of the invention may be used in the preparation of a food composition, for example an ice cream or a sorbet.

Use of the ISP of the invention confers a number of advantages either on the final food composition or in the preparation of such a composition.

In relation to the preparation of a food composition, for example, use of an ISP of the invention allows slower hardening in the preparation of a frozen food composition, for example in the preparation of an ice cream or sorbet. This may allow the use of larger package sizes and/or the use of less power input in blast freezing during hardening. In addition, the use of ISP of the invention may even lead to the omission of the hardening step during ice cream and frozen dessert production, allowing a faster production process with less energy costs. In addition, the use of an ISP of the invention may enable decreased use of stabilizers during the preparation of a food composition, such as an ice cream or a sorbet.

In relation to a food composition itself as prepared using an ISP of the invention, such a food composition may have an increased shelf life without quality loss (as compared to a corresponding food composition prepared without use of an ISP of the invention). In particular, a food composition prepared using an ISP of the invention may be more resistant to heat shock that a food composition not prepared with such as ISP and it may be possible to store such a food composition at a higher temperature than a food composition not prepared with such an ISP. The quality of such food composition may be less vulnerable to the temperature fluctuations that accompany transport and retail handling of such food product Further, the resulting food composition as prepared using an ISP of the invention may have improved textural properties, for example the resulting food composition may be more firm with higher overrun so that less ingredients may be required in preparation of such food composition, and melting may be decreased such that there is less dripping (again in comparison with an equivalent food composition not made with an ISP of the invention).

Accordingly, the invention relates to a nucleic acid construct comprising a nucleic acid sequence encoding an ice structuring protein (ISP) and, linked operably thereto, control sequences permitting expression of the nucleic acid sequence in a filamentous fungal host cell. The nucleic acid construct may be incorporated into a vector, such as an expression vector and/or into a host cell in order to effect expression of the ISP.

The term "nucleic acid construct" is herein referred to as a nucleic acid molecule, either single-or double-stranded, which is isolated from a naturally-occurring gene or, more typically, which has been modified to contain segments of nucleic acid which are combined and juxtaposed in a manner which would not otherwise exist in nature. That is to say, a nucleic acid construct according to the invention is a recombinant construct. i.e. one which is non-naturally occurring. The term nucleic acid construct is synonymous with the term "expression cassette" when the nucleic acid construct contains all the control sequences required for expression of a coding sequence, wherein said control sequences are operably linked to said coding sequence.

A nucleic acid construct of the invention comprises a nucleic acid sequence encoding an ice structuring protein (ISP).

For the purposes of this invention, "ice structuring protein (ISP)" or, alternatively, "antifreeze protein (AFP)" or "ice binding protein" refers to a polypeptide capable of binding small ice crystals so as to inhibit growth and recrystallization of ice crystals. Recrystallization inhibition (RI) can be measured as described in Example 4 (see Tomczak et al (2003) Biochem. Biophys. Res. Comm. 311: 1041-1046).

An ISP may also, or alternatively, be a polypeptide which is capable of creating or increasing the difference between the melting point and freezing point of a solution, i.e. is one which is capable of increasing the thermal hysteresis of a solution, in comparison with the same solution not comprising an ISP. Thermal hysteresis may be measured with a Clifton nanolitre osmometer.

The nucleic acid sequence (comprised within a nucleic acid construct of the invention) encodes an ISP comprising:

the amino acid sequence set out in SEQ ID NO: 1 or a sequence at least 80% identical thereto; or the amino acid sequence set out in amino acids 21 to 261 of SEQ ID NO: 1 or a sequence at least 50%, 60%, 70% or 80% identical thereto.

SEQ ID NO: 1 sets out the protein sequence of the ISP of *Leucosporidium* (AFP19). This sequence consists of a signal sequence of 20 amino acids for efficient secretion in *Leucosporidium* and a deduced mature protein sequence of 241 amino acids.

In a nucleic acid construct of the invention, the nucleic acid sequence may encode an ISP comprising the sequence set out in SEQ ID NO: 1 or a sequence at least 85%, at least 90%, at least 95%, at least 98% or at least 99% identical thereto or comprising the sequence set out in amino acids 21 to 261 of SEQ ID NO: 1 or a sequence at least 85%, at least 90%, at least 95%, at least 98% or at least 99% identical thereto.

That is to say, the nucleic acid sequence used in a nucleic acid construct of the invention may share at least 50%, 60%, 70%, 80%, at least 85%, at least 90%, at least 95%, at least 97%, at least 98%, at least 99% sequence identity with either of the amino acid sequence set out in SEQ ID NO: 1 or the amino acid sequence set out in amino acids 21 to 261 of SEQ ID NO: 1.

In a nucleic acid construct of the invention, the nucleic acid may encodes an ISP comprising an amino acid sequence obtainable from an arctic yeast of the genus *Leucosporidium*.

For the purpose of this invention, it is defined here that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

The amino acid sequence of the ISP which is actually expressed in a filamentous fungi may not comprise all of those amino acids theoretically encoded by the nucleic acid sequence. For example, the amino acid sequence may be shorter than that theoretically encoded by the nucleic acid sequence, for example in view of amino acids missing from the N- and/or C-terminal ends of the ISP (in comparison with the predicted sequence). For example, the amino acid sequence may be one, two, three, four, five, six, seven, eight, nine, ten, eleven or twelve or more amino acids shorter than the predicted mature sequence of amino acids 21 to 261 of SEQ ID NO: 1. In this case, identity may be calculated on the basis of an alignment which excludes those amino acids theoretically, but not actually, present.

Thus, a nucleic acid sequence (comprised within a nucleic acid construct of the invention) may encode an ISP comprising:

the amino acid sequence set out in amino acids 21 to 260 of SEQ ID NO: 1, amino acids 21 to 259 of SEQ ID NO: 1, amino acids 21 to 258 of SEQ ID NO: 1, amino acids 21 to 257 of SEQ ID NO: 1, amino acids 21 to 256 of SEQ ID NO: 1, amino acids 21 to 255 of SEQ ID NO: 1, amino acids 21 to 254 of SEQ ID NO: 1, amino acids 21 to 253 of SEQ ID NO: 1, amino acids 21 to 252 of SEQ ID NO: 1, amino acids 21 to 251 of SEQ ID NO: 1, amino acids 21 to 250 of SEQ ID NO: 1, amino acids 21 to 249 of SEQ ID NO: 1, amino acids 21 to 248 of SEQ ID NO: 1, amino acids 21 to 247 of SEQ ID NO: 1 or amino acids 21 to 246 of SEQ ID NO: 1 or a sequence at least 50%, at least 60%, at least 70%, at least 80%, at least 85%, at least 90%, at least 95%, at least 98% or at least 99% identical to any one thereto.

In another preferred option, the amino acid sequence of the ISP has been modified resulting in a further improved expression in a filamentous fungi according the method as described in WO2010/102982.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percentage of sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information ncbi.nlm.nih.gov.

The nucleic acid sequence encoding an ISP is operably linked to control sequences permitting expression of the said nucleic acid sequence in a filamentous fungal host cell.

The term "operably linked" is defined herein as a configuration in which a control sequence is appropriately placed at a position relative to the ISP coding sequence such that the control sequence directs the production of an RNA or an mRNA and optionally of a polypeptide translated from said (m)RNA.

The term "control sequences" is defined herein to include all components, which are necessary or advantageous for the expression of mRNA and/or a polypeptide, either in vitro or in a host cell. Each control sequence may be native or foreign to the nucleic acid sequence encoding the polypeptide. Such control sequences include, but are not limited to, a leader, Shine-Delgarno sequence, optimal translation initiation sequences (as described in Kozak, 1991, J. Biol. Chem. 266:19867-19870), a polyadenylation sequence, a pro-peptide sequence, a pre-pro-peptide sequence, a promoter, a signal sequence, and a transcription terminator. Signal sequences used for optimizing expression are described in WO2010/121933. At a minimum, the control sequences include a promoter, and transcriptional and translational stop signals. Control sequences may be optimized to their specific purpose. Preferred optimized control sequences used in the present invention are those described in WO2006/077258, which is herein incorporated by reference.

One or more control sequences may be a control sequence which does not natively occur in *Leucosporidium*, for example a *Leucosporidium* from which the ISP was originally isolated.

The control sequences may be provided with linkers for the purpose of introducing specific restriction sites facilitating ligation of the control sequences with the coding region of the nucleic acid sequence encoding a polypeptide.

The control sequence may be an appropriate promoter sequence (promoter). The term "promoter" is defined herein as a DNA sequence that binds RNA polymerase and directs the polymerase to the correct downstream transcriptional start site of the nucleic acid sequence encoding an ISP. RNA polymerase effectively catalyzes the assembly of messenger RNA complementary to the appropriate DNA strand of a coding region. The term "promoter" will also be understood to include the 5'-non-coding region (between promoter and translation start) for translation after transcription into mRNA, cis-acting transcription control elements such as enhancers, and other nucleotide sequences capable of interacting with transcription factors.

A nucleic acid construct of the invention may be one wherein the control sequences comprise a promoter not natively associated with the nucleic acid encoding an ISP.

The promoter may be any appropriate promoter sequence suitable for a filamentous fungus host cell, which shows transcriptional activity, including mutant, truncated, and hybrid promoters, and may be obtained from polynucleotides encoding extra-cellular or intracellular polypeptides either homologous (native) or heterologous (foreign) to the filamentous fungal host cell. The promoter may be a constitutive or inducible promoter.

The promoter may be an inducible promoter. The promoter may be a carbohydrate inducible promoter. Carbohydrate inducible promoters that can be used are a starch-, cellulose-, hemicellulose (such as xylan- and/or xylose-inducible) promoters. Other inducible promoters are copper-, oleic acid-inducible promoters. Promoters suitable in filamentous fungi are promoters which may be selected from the group, which includes but is not limited to promoters obtained from the polynucleotides encoding *A. oryzae* TAKA amylase, *Rhizomucor miehei* aspartic proteinase, *A. niger* neutral alpha-amylase, *A. niger* acid stable alpha-amylase, *A. niger* or *A. awamori* glucoamylase (glaA), *A. niger* or *A. awamori* endoxylanase (xlnA) or beta-xylosidase (xlnD), *T. reesei* cellobiohydrolase I (CBHI), *R. miehei* lipase, *A. oryzae* alkaline protease, *A. oryzae* triose phosphate isomerase, *A. nidulans* acetamidase, *Fusarium venenatum* amyloglucosidase (WO 00/56900), *Fusarium venenatum* Dania (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the polynucleotides encoding *A. niger* neutral alpha-amylase and *A. oryzae* triose phosphate isomerase), and mutant, truncated, and hybrid promoters thereof. Other examples of promoters are the promoters described in WO2006/092396 and WO2005/100573, which are herein incorporated by reference. An even other example of the use of promoters is described in WO2008/098933 and PCT/EP2-13/062490. Promoters can also be constitutive promoters.

The control sequence may also be a suitable transcription terminator (terminator) sequence, a sequence recognized by a filamentous fungal cell to terminate transcription. The terminator sequence is operably linked to the 3'-terminus of the nucleic acid sequence encoding the polypeptide. Any terminator, which is functional in the cell, may be used in the present invention. The man skilled in the art knows which types of terminators can be used in the microbial host cell as described herein.

Preferred terminator sequences for filamentous fungal cells are obtained from any terminator sequence of a filamentous fungal gene, more preferably from *Aspergillus* genes, even more preferably from the gene *A. oryzae* TAKA amylase, the genes encoding *A. niger* glucoamylase (glaA), *A. nidulans* anthranilate synthase, *A. niger* alpha-glucosidase, trpC and/or *Fusarium oxysporum* trypsin-like protease.

The control sequence may also be an optimal translation initiation sequences (as described in Kozak, 1991, J. Biol. Chem. 266:19867-19870), or a 5'-untranslated sequence, a non-translated region of a mRNA which is important for translation by filamentous fungal host cell. The translation initiation sequence or 5'-untranslated sequence is operably linked to the 5'-terminus of the coding sequence encoding the polypeptide. Each control sequence may be native or foreign to the nucleic acid sequence encoding the polypeptide. Control sequences may be optimized to their specific purpose.

Suitable 5'-untranslated sequences may be those polynucleotides preceeding the fungal amyloglucosidase (AG) gene, *A. oryzae* TAKA amylase and *Aspergillus* triose phosphate isomerase genes and *A. niger* glucoamylase glaA, alpha-amylase, xylanase and phytase encoding genes.

The control sequence may also be a non-translated region of a mRNA which is important for translation by the filamentous fungus host cell.

A leader (or signal) sequence may be operably linked to the 5'-terminus of the nucleic acid sequence encoding the polypeptide. Any leader, which is functional in the cell, may be used in the present invention. Leader sequences may be those originating from the fungal amyloglucosidase (AG) gene (glaA-both 18 and 24 amino acid versions e. g. from *Aspergillus*), the α-factor gene (yeasts e.g. *Saccharomyces* and *Kluyveromyces*) or the α-amylase (amyE, amyQ and amyL) and alkaline protease aprE and neutral protease genes (*Bacillus*), or signal sequences as described in WO2010/121933.

Preferred leaders (or signal sequences) for filamentous fungal cells are obtained from the polynucleotides preceding *A. oryzae* TAKA amylase and *A. niger* glaA and phytase.

Other control sequences may be isolated from the *Penicillium* IPNS gene, or pcbC gene, the beta tubulin gene. All the control sequences cited in WO 01/21779 are herewith incorporated by reference.

The control sequence may also be a polyadenylation sequence, a sequence which is operably linked to the 3'-terminus of the nucleic acid sequence and which, when transcribed, is recognized by the microbial host cell (mutated or parent) as a signal to add polyadenosine residues to transcribed mRNA. Any polyadenylation sequence, which is functional in the cell, may be used in the present invention.

Preferred polyadenylation sequences for filamentous fungal cells are obtained from the polynucleotides encoding *A. oryzae* TAKA amylase, *A. niger* glucoamylase, *A. nidulans* anthranilate synthase, *Fusarium oxysporum* trypsin-like protease and *A. niger* alpha-glucosidase.

In order to facilitate expression, the nucleic acid sequence encoding the ISP may be a synthetic polynucleotide. Synthetic polynucleotides may be optimized in codon use, preferably according to the methods described in WO2006/077258 and/or PCT/EP2007/055943 (published as WO2008/000632), which are herein incorporated by reference. PCT/EP2007/055943 addresses codon-pair optimization. Codon-pair optimization is a method wherein the nucleotide sequences encoding a polypeptide have been modified with respect to their codon-usage, in particular the codon-pairs that are used, to obtain improved expression of the nucleotide sequence encoding the ISP and/or improved production of the encoded ISP. Codon pairs are defined as a set of two subsequent triplets (codons) in a coding sequence.

Accordingly, a nucleic acid construct of the invention may be one wherein the nucleic acid encoding an ISP is codon pair optimized for expression in a filamentous fungal host cell.

In order to facilitate expression and/or translation of the ISP, the nucleic acid sequence encoding the ISP may be comprised in an expression vector such that the gene encoding the ISP is operably linked to the appropriate control sequences for expression and/or translation in vitro, or in the filamentous fungal host cell. That is to say, the invention provides an expression vector comprising a nucleic acid construct of the invention.

The expression vector may be any vector (e.g., a plasmid or virus), which can be conveniently subjected to recombinant DNA procedures and can bring about the expression of the polynucleotide encoding the polypeptide. The choice of the vector will typically depend on the compatibility of the vector with the cell into which the vector is to be introduced. The vectors may be linear or closed circular plasmids. The vector may be an autonomously replicating vector, i. e., a vector, which exists as an extra-chromosomal entity, the replication of which is independent of chromosomal replication, e.g., a plasmid, an extra-chromosomal element, a mini-chromosome, or an artificial chromosome. An autonomously maintained cloning vector may comprise the AMA1-sequence (see e.g. Aleksenko and Clutterbuck (1997), Fungal Genet. Biol. 21: 373-397).

Alternatively, the vector may be one which, when introduced into the filamentous fungal host cell, is integrated into the genome and replicated together with the chromosome(s) into which it has been integrated. The integrative cloning vector may integrate at random or at a predetermined target locus in the chromosomes of the host cell. In a preferred embodiment of the invention, the integrative cloning vector comprises a DNA fragment, which is homologous to a DNA sequence in a predetermined target locus in the genome of host cell for targeting the integration of the cloning vector to this predetermined locus. In order to promote targeted integration, the cloning vector is preferably linearized prior to transformation of the cell. Linearization is preferably performed such that at least one but preferably either end of the cloning vector is flanked by sequences homologous to the target locus. The length of the homologous sequences flanking the target locus is preferably at least 30 bp, preferably at least 50 bp, preferably at least 0.1 kb, even preferably at least 0.2 kb, more preferably at least 0.5 kb, even more preferably at least 1 kb, most preferably at least 2 kb. Preferably, the efficiency of targeted integration into the genome of the filamentous fungus host cell, i.e. integration in a predetermined target locus, is increased by augmented homologous recombination abilities of the host cell.

Preferably, the homologous flanking DNA sequences in the cloning vector, which are homologous to the target locus, are derived from a highly expressed locus meaning that they are derived from a gene, which is capable of high expression level in the host cell. A gene capable of high expression level, i.e. a highly expressed gene, is herein defined as a gene whose mRNA can make up at least 0.5% (w/w) of the total cellular mRNA, e.g. under induced conditions, or alternatively, a gene whose gene product can make up at least 1% (w/w) of the total cellular protein, or, in case of a secreted gene product, can be secreted to a level of at least 0.1 g/l (as described in EP 357 127 B1).

A number of preferred highly expressed fungal genes are given by way of example: the amylase, glucoamylase, alcohol dehydrogenase, xylanase, glyceraldehyde-phosphate dehydrogenase or cellobiohydrolase (cbh) genes from *Aspergilli*, *Chrysosporium* or *Trichoderma*. Most preferred highly expressed genes for these purposes are a glucoamylase gene, preferably an *A. niger* glucoamylase gene, an *A. oryzae* TAKA-amylase gene, an *A. nidulans* gpdA gene, a *Trichoderma reesei* cbh gene, preferably cbh1, a *Chrysosporium lucknowense* cbh gene or a cbh gene from *P. chrysogenum*.

More than one copy of a nucleic acid construct of the invention may be inserted into a filamentous fungus host cell to increase production of the ISP (over-expression) encoded by the nucleic acid sequence comprised within the nucleic acid construct. This can be done, preferably by integrating into its genome copies of the DNA sequence, more preferably by targeting the integration of the DNA sequence at one of the highly expressed loci defined in the former paragraph. Alternatively, this can be done by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent. To increase even more the number of copies of the DNA sequence to be over expressed the technique of gene conversion as described in WO98/46772 may be used.

The vector system may be a single vector or plasmid or two or more vectors or plasmids, which together contain the total DNA to be introduced into the genome of the host cell, or a transposon.

The vectors preferably contain one or more selectable markers, which permit easy selection of transformed cells. A selectable marker is a gene the product of which provides for biocide or viral resistance, resistance to heavy metals, prototrophy to auxotrophs, and the like. The selectable marker may be introduced into the cell on the expression vector as the expression cassette or may be introduced on a separate expression vector.

A selectable marker for use in a filamentous fungal cell may be selected from the group including, but not limited to, amdS (acetamidase), argB (ornithine carbamoyltransferase), bar (phosphinothricinacetyltransferase), bleA (phleomycin binding), hygB (hygromycinphosphotransferase), niaD (nitrate reductase), pyrG (orotidine-5'-phosphate decarboxylase), sC (sulfate adenyltransferase), NAT or NTC (Nourseothricin) and trpC (anthranilate synthase), as well as equivalents from other species. Preferred for use in an *Aspergillus* and *Penicillium* cell are the amdS (see for example EP 635574 B1, EP0758020A2, EP1799821A2, WO 97/06261A2) and pyrG genes of *A. nidulans* or *A. oryzae* and the bar gene of *Streptomyces hygroscopicus*. More preferably an amdS gene is used, even more preferably an amdS gene from *A. nidulans* or *A. niger*. A most preferred selectable marker gene is the *A. nidulans* amdS coding sequence fused to the *A. nidulans* gpdA promoter (see EP 635574 B1). Other preferred AmdS markers are those described in WO2006/040358. AmdS genes from other filamentous fungi may also be used (WO 97/06261).

Preferably, any selection marker is deleted from the transformed filamentous fungus host cell after introduction of the expression construct so as to obtain transformed host cells capable of producing the ISP which are free of selection marker genes.

The procedures used to ligate the elements described above to construct the expression vectors of the present invention are well known to one skilled in the art (see, e.g. Sambrook & Russell, *Molecular Cloning: A Laboratory Manual*, 3rd Ed., CSHL Press, Cold Spring Harbor, N.Y., 2001; and Ausubel et al., *Current Protocols in Molecular Biology*, Wiley InterScience, NY, 1995).

Furthermore, standard molecular cloning techniques such as DNA isolation, gel electrophoresis, enzymatic restriction modifications of nucleic acids, Southern analyses, transformation of cells, etc., are known to the skilled person and are for example described by Sambrook et al. (1989) "Molecular Cloning: a laboratory manual", Cold Spring Harbor Laboratories, Cold Spring Harbor, N.Y. and Innis et al. (1990) "PCR protocols, a guide to methods and applications" Academic Press, San Diego.

A nucleic acid suitable for use in the invention may be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis.

Preferably, the efficiency of targeted integration into the genome of the host cell, i.e. integration in a predetermined target locus, is increased by augmented homologous recombination abilities of the host cell. Such phenotype of the cell preferably involves a deficient hdfA or hdfB as described in WO2005/095624. WO2005/095624 discloses a preferred method to obtain a filamentous fungal cell comprising increased efficiency of targeted integration The invention thus provides a filamentous fungal host cell which comprises a nucleic acid construct or an expression vector of the invention.

The filamentous fungal host cell may be a cell of any filamentous form of the subdivision Eumycota and Oomycota (as defined by Hawksworth et al., In, Ainsworth and Bisby's Dictionary of The Fungi, 8th edition, 1995, CAB International, University Press, Cambridge, UK). The filamentous fungi are characterized by a mycelial wall composed of chitin, cellulose, glucan, chitosan, mannan, and other complex polysaccharides. Vegetative growth is by hyphal elongation and carbon catabolism is obligately aerobic.

The filamentous fungal host cell may be a cell of any filamentous form of the taxon Trichocomaceae (as defined by Houbraken and Samson in Studies in Mycology 70: 1-51. 2011). In another preferred embodiment, the filamentous fungal host cell may be a cell of any filamentous form of any of the three families Aspergillaceae, Thermoascaceae and Trichocomaceae, which are accommodated in the taxon Trichocomaceae. Suitable filamentous fungal host cells may be those in Clade 2: *Aspergillus* as described in FIG. 1 of Houbraken and Samson, 2011 (supra).

Suitable filamentous fungal host cells suitable for use in the invention include, but are not limited to, cells of *Acremonium, Agaricus, Aspergillus, Aureobasidium, Chrysosporium, Coprinus, Cryptococcus, Filibasidium, Fusarium, Humicola, Magnaporthe, Mucor, Myceliophthora, Neocallimastix, Neurospora, Paecilomyces, Penicillium, Piromyces, Panerochaete, Pleurotus, Schizophyllum, Talaromyces, Rasamsonia, Thermoascus, Thielavia, Tolypocladium,* and *Trichoderma*.

Preferred filamentous fungal cells belong to a species of an *Acremonium, Aspergillus, Chrysosporium, Myceliophthora, Penicillium, Talaromyces, Rasamsonia, Thielavia, Fusarium* or *Trichoderma* genus, and most preferably a species of *Aspergillus niger, Acremonium alabamense, Aspergillus awamori, Aspergillus foetidus, Aspergillus sojae, Aspergillus fumigatus, Talaromyces emersonii, Rasamsonia emersonii, Aspergillus oryzae, Chrysosporium lucknowense, Fusarium oxysporum, Fusarium venenatum, Myceliophthora thermophila, Trichoderma reesei, Thielavia terrestris* or *Penicillium chrysogenum*. A more preferred host cell belongs to the genus *Aspergillus*, more preferably the host cell belongs to the species *Aspergillus niger*. When the host cell according to the invention is an *Aspergillus niger* host cell, the host cell preferably is CBS 513.88, CBS124.903 or a derivative thereof.

Several strains of filamentous fungi are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), Agricultural Research Service Patent Culture Collection, Northern Regional Research Center (NRRL), and All-Russian Collection of Microorganisms of Russian Academy of Sciences, (abbreviation in Russian—VKM, abbreviation in English—RCM), Moscow, Russia. Useful strains in the context of the present invention may be *Aspergillus niger* CBS 513.88, CBS124.903, *Aspergillus oryzae* ATCC 20423, IFO 4177, ATCC 1011, CBS205.89, ATCC 9576, ATCC14488-14491, ATCC 11601, ATCC12892, *P. chrysogenum* CBS 455.95, *P. chrysogenum* Wisconsin54-1255 (ATCC28089), *Penicillium citrinum* ATCC 38065, *Penicillium chrysogenum* P2, *Rasamsonia emersonii* ATCC16479, CBS393.64, IFO31232, IMI116815, *Thielavia terrestris* NRRL8126, *Talaromyces emersonii* CBS 124.902, *Acremonium chrysogenum* ATCC 36225 or ATCC 48272, *Trichoderma reesei* ATCC 26921 or ATCC 56765 or ATCC 26921, *Aspergillus sojae* ATCC11906, *Myceliophthora thermophila* C1, Garg 27K, VKM-F 3500 D, *Chrysosporium lucknowense* C1, Garg 27K, VKM-F 3500 D, ATCC44006 and derivatives thereof.

Preferred filamentous fungus host cells such as *A. niger* host cells, for example possibly contain one, more or all of the following modifications: deficient in a non-ribosomal peptide synthase preferably deficient in a non-ribosomal peptide synthase npsE (see WO2012/001169), deficient in pepA, deficient in glucoamylase (glaA), deficient in acid stable alpha-amylase (amyA), deficient in neutral alpha-amylase (amyBI and amyBII), deficient in oxalic acid hydrolase (oahA), deficient in one or more toxins, preferably ochratoxin and/or fumonisin, deficient in prtT, deficient in hdfA, comprises a SEC 61 modification being a S376W mutation in which Serine 376 is replaced by Tryptophan and/or comprises an adapted amplicon as defined in WO2005/123763 and/or WO2011/009700. These and other possible host modifications are also described in WO2012/001169, WO2011/009700, WO2007/062936, WO2006/040312 or WO2004/070022, WO2013/135729, WO2014/013074, WO2014/013073.

Those skilled in the art know how to transform cells with the one or more nucleic acid construct or expression vector of the invention.

Transformation of the filamentous fungal host cell may be conducted by any suitable known methods, including e.g. electroporation methods, particle bombardment or microprojectile bombardment, protoplast methods and *Agrobacterium* mediated transformation (AMT). Procedures for transformation are described by J. R. S. Fincham, Transformation in fungi. 1989, Microbiological reviews. 53, 148-170.

Transformation may involve a process consisting of protoplast formation, transformation of the protoplasts, and regeneration of the cell wall in a manner known per se. Suitable procedures for transformation of *Aspergillus* cells are described in EP 238 023 and Yelton et al., 1984, Proceedings of the National Academy of Sciences USA 81:1470-1474. Suitable procedures for transformation of

*Aspergillus* and other filamentous fungal host cells using *Agrobacterium tumefaciens* are described in e.g. De Groot et al., *Agrobacterium tumefaciens*-mediated transformation of filamentous fungi. Nat Biotechnol. 1998, 16:839-842. Erratum in: Nat Biotechnol 1998 16:1074. A suitable method of transforming *Fusarium* species is described by Malardier et al., 1989, Gene 78:147156 or in WO 96/00787. Other methods can be applied such as a method using biolistic transformation as described in: Christiansen et al., *Biolistic transformation of the obligate plant pathogenic fungus, Erysiphe graminis* fsp. *hordei*. 1995, Curr Genet. 29:100-102.

The invention further provides a method for the production of an ice structuring protein (ISP), which method comprises:

a. providing a filamentous fungal host cell which comprises a nucleic acid sequence encoding an ISP comprising the sequence set out in SEQ ID NO: 1 or a sequence at least 80% identical thereto or comprising the sequence set out in amino acids 21 to 261 of SEQ ID NO: 1 or a sequence at least 80% identical thereto, wherein the said nucleic acid sequence is operably linked to control sequences permitting expression of the nucleic acid sequence in the filamentous fungal host cell;

b. cultivating the filamentous fungal host cell under conditions suitable for production of the ice structuring protein; and, optionally c. recovering the ice structuring protein.

Typically, the ISP is secreted from the host cell, for example during the cultivation step.

In step a. a mutant microbial host cell may be a filamentous fungus host cell of the invention as described herein.

In step b. the filamentous fungus host cell of step a. is cultured under conditions conducive to the expression of the ISP. The mutant microbial cells are cultivated in a nutrient medium suitable for production of the ISP using methods known in the art. For example, the cells may be cultivated by shake flask cultivation, small-scale or large-scale fermentation (including continuous, batch, fed-batch, or solid state fermentations) in laboratory or industrial fermentors performed in a suitable medium and under conditions allowing the ISP to be produced and/or isolated. The cultivation takes place in a suitable nutrient medium comprising carbon and nitrogen sources and inorganic salts, using procedures known in the art (see, e. g., Bennett, J. W. and LaSure, L., eds., *More Gene Manipulations in Fungi*, Academic Press, CA, 1991). Suitable media are available from commercial suppliers or may be prepared using published compositions (e. g., in catalogues of the American Type Culture Collection).

If the ISP is secreted into the nutrient medium, the ISP can be isolated directly from the medium. If the ISP is not secreted, it can be isolated from cell lysates.

In step c., the ISP may be optionally isolated. The ISP may be isolated by methods known in the art. For example, the ISP may be isolated from the nutrient medium by conventional procedures including, but not limited to, centrifugation, filtration, extraction, spray drying, evaporation, or precipitation. The isolated ISP may then be further purified by a variety of procedures known in the art including, but not limited to, chromatography (e. g., ion exchange, affinity, hydrophobic, chromatofocusing, and size exclusion), electrophoretic procedures (e.g., preparative isoelectric focusing), differential solubility (e. g., ammonium sulfate precipitation), or extraction (see, e.g., *Protein Purification*, J.-C. Janson and Lars Ryden, editors, VCH Publishers, New York, 1989). In some applications the ISP may be used without substantial isolation from the culture broth; separation of the culture medium from the biomass may be adequate.

In a method of the invention, productivity of the ISP may be at least 1 g/L, at least 2 g/L, at least 5 g/L, such as 10 g/L or higher.

The invention further provides an ice structuring protein obtainable by a method of the invention as described herein.

The invention further provides an ice structuring protein obtainable by a method of the invention as described herein.

The invention also provides an ice structuring protein comprising the sequence set out in SEQ ID NO: 1 or a sequence at least 80% identical thereto or comprising the sequence set out in amino acids 21 to 261 of SEQ ID NO: 1 or a sequence at least 80% identical thereto, wherein:

at least one amino acid is a modified amino acid, for example comprising a pyroglutamate modification at its N-terminus;

at least one amino acid is O-mannosylated, for example comprising one, two, three, four or more O-mannosylations;

the protein has a glycosylation pattern other than 2GlcNac and 2 hexose units, for example 2GlcNac and three, four, five, six, seven, eight, nine, ten or more hexose units; or the protein lacks VVQKRSNARQWL (SEQ ID NO:4), VQKRSNARQWL (SEQ ID NO:5),and KRSNARQWL (SEQ ID NO:6),at the C-terminus.

That is to say, the protein may have a C-terminal truncation of one, two, three, four, five, six, seven, eight, nine, ten, eleven or twelve or more amino acids with reference to the protein set out in SEQ ID NO: 1.

In such an ice structuring protein, the modified amino acid may be a pyroglutamate, optionally present at the N-terminus of the protein (i.e. at an amino acid corresponding to amino acid 21 in SEQ ID NO: 1).

An ice structuring protein of the invention may comprise 2 N-acetylglucosamine (GlcNAc) and 10 hexose (Hex) units. An ice structuring protein of the invention may be O-mannosylated at a position corresponding to S80 and/or T84 with reference to SEQ_ID NO:1. The most abundant form of AFP19 contains one O-mannosyl group.

An ISP of the invention may comprise the amino acid sequence set out in SEQ ID NO: 1 or a sequence at least 85%, at least 90%, at least 95%, at least 98% or at least 99% identical thereto or comprising the sequence set out in amino acids 21 to 261 of SEQ ID NO: 1 or a sequence at least 85%, at least 90%, at least 95%, at least 98% or at least 99% identical thereto.

The ISP of the invention, for example as obtainable by a method of the invention, may be used in the preparation of a food composition. Accordingly, the invention provides a food composition comprising an ISP of the invention, for example as obtainable by a method of the invention.

Preferred food compositions are frozen confectionery products, such as ice-cream, frozen yoghurt, frozen desserts, sherbet, sorbet, ice milk, frozen custard, water-ices, granitas and frozen fruit purees, soft serve, frappé, slush, smoothies, shave ice, snow cones, semifreddo, milk shakes or gelato.

The level of ISP may be from 0.00001 to 0.5% by weight based on the final composition.

A food composition of the invention, such as a frozen confectionary product, the level of solids in the frozen confection (e.g. sugars, fats, flavourings etc) may be more than 4% by weight, for example more than 20% by weight, such as from 20% to 60%, for example 30% to 45% by weight based on the final composition.

In the case of an ice cream composition, for example, illustrative ingredients and amounts thereof are as follows:

Water may be from 40 to 80% by weight of the composition.

The sweetening agent may be from 5-30%, from 10-25% or from 15-20% by weight of the composition. Low calorie sweetening agents such as sucralose, saccharin or aspartame may be used as sweetening agents as may one or more sugars. The term sugar includes a monosaccharide, a disaccharide, a polysaccharide, a sugar alcohol, or a mixture thereof monosaccharide is a chemical compound of general formula $C_nH_{2n}O_n$ where n=3-7, and disaccharide is a condensation product of any two identical or different monosaccharides. Suitable monosaccharides include glucose and fructose. A suitable disaccharide is sucrose. Sweetening agents also include corn syrups (also called glucose syrups), which are mixtures of mono-, di- and higher saccharides and sugar alcohols.

Milk solids may be from 5 to 40% by weight of the composition. Milk solids include non-fat milk solids (lactose, milk protein and minerals) and milk fat (also called butter fat). Milk solids may be present in an amount of at least 10%, such as at least 15%, for example 20% by weight of the composition. The composition may comprise up to 35%, up to 30% or up to 25% milk solids. Milk solids may be added to the composition in form of milk powder. Alternatively, fresh milk or Pasteurized milk may be added to the composition to provide the requisite amount of milk solids.

An ice cream composition may comprise fat. In this case, the fat may be from 2-20%, from 4-18% or from 6-16% by weight of the composition. The fat may by a vegetable fat and/or milk fat.

An ice cream composition may comprise 1-10%, such as 2-9%, for example 3-8% protein. Protein may be a wheat protein, soya protein, or milk protein.

An ice cream composition may comprise other optional ingredients including flavours, fruit/vegetable, and chocolate.

An ISP of the invention may be combined with one or more food ingredients so as to prepare a food composition of the invention. That is to say, the invention provides a method for the preparation of a food composition, which method comprises combining an ice structuring protein of the invention with one or more food ingredients, thereby to prepare a food composition.

Frozen confectionery products according to the invention can be produced by any method suitable for the production of frozen confectionery. Typically, all the ingredients of the composition are fully mixed before the freezing process starts. The freezing process may advantageously involve a hardening step, for example to a temperature of −30° C. or lower.

The invention also provides use of an ice structuring protein of the invention in a food composition.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

Example 1

Cloning and Expression of the AFP19 Gene

The protein sequence of the ISP of *Leucosporidium* (AFP19) was deduced from the published gene sequence and is shown in SEQ ID NO: 1. This sequence consists of a signal sequence of 20 amino acids for efficient secretion in *Leucosporidium*, and a deduced mature protein sequence of 241 amino acids.

A codon-adapted DNA sequence for expression of this protein in *Aspergillus niger* was designed containing additional restriction sites for subcloning in an *Aspergillus* expression vector. Codon adaptation was performed as described in WO2008/000632. The DNA sequence of the gene encoding the ISP protein of SEQ ID NO:1 is shown in SEQ ID NO: 2.

The translational initiation sequence of the glucoamylase glaA promoter has been modified into 5'-CACCGTCAAA ATG-3' and an optimal translational termination sequence 5'-TAAA-3' was used in the generation of the expression construct (as also detailed in WO2006/077258). A DNA fragment (SEQ ID NO: 3), containing a.o. part of the glucoamylase promoter and the ISP encoding gene, was synthesized completely, purified and digested with EcoRI and PacI. The pGBTOP-16 vector (FIG. 1) was linearized by EcoRI/PacI digestion and the linearized vector fragment was subsequently purified by gel-extraction. The DNA fragment was cloned into the pGBTOP-16 vector and the resulting vector was named pGBTOPAFP-19. Subsequently, *A. niger* GBA 306 was transformed with this pGBTOPAFP-19 vector, in a co-transformation protocol with pGBAAS-4, with strain and methods as described in WO 2011/009700 and references therein, and selected on acetamide containing media and colony purified according to standard procedures. *A. niger* GBA306 is ultimately derived from CBS124.903 (deposited at the Centraalbureau voor Schimmelcultures, Utrecht, the Netherlands) Transformation and selection was performed as described in WO 98/46772 and WO 99/32617. Strains containing the AFP19 gene were selected via PCR with primers specific for the AFP19 gene to verify presence of the pGBTOPAFP-19 expression cassette. A single transformant was selected, named AFP19-3, and further replicaplated to obtain a single strain inoculum.

Example 2

Fermentation and Purification of AFP19 in *Aspergillus niger*

Fresh *A. niger* AFP19-3 spores were prepared. 4 shake flasks with 100 ml Fermentation medium 1 (10% w/v Corn Steep Solids, 1% w/v glucose.$H_2O$, 0.1% w/v $NaH_2PO_4.H_2O$, 0.05% w/v $MgSO_4.7H_2O$, 0.025% w/v Basildon, pH 5.8) in 500 ml shake flasks with baffle were inoculated with $10^7$ spores. These pre-cultures were incubated at 34° C. and 170 rpm for 16-24 hours. From the pre-cultures, 50 ml was used for inoculation of 4 shake flasks with 1 liter Fermentation medium 2 (15% w/v maltose, 6% w/v bacto-soytone, 1.5% w/v $(NH_4)_2SO_4$, 0.1% w/v $NaH_2PO_4.H_2O$, 0.1% w/v $MgSO_4.7H_2O$, 0.1% w/v L-arginine, 8% w/v Tween-80, 2% w/v Basildon, 2% w/v MES pH 5.1) in a 5 liter shake flask size and shaken at 34° C. and 170 rpm. After four days of cultivation, the cells were killed off by adding 3.5 g/l of sodium benzoate and keeping at 30° C. for six hours. Subsequently, 10 g/l CaCl2 and 45 g/l Perlite C25 was added to the culture broth. Filtration was carried out in one step using filter cloth and filters DE60/EKS P and K250 (Pall). The filter cake remaining at the filter was washed with 1.1 l of sterile milliQ water. Subsequent sterile filtration was carried out using 0.22 m GP Express PLUS Membrane (Millipore). Ultrafiltration was carried out on the Pellicon 2 "mini" ultrafiltration system with the cassette Biomax5k (Millipore) and washed with 50 mM Na-acetate, pH 5.6. The protein composition of purified samples at all steps was controlled by 4-12% SDS-PAGE and found to be >90% pure AFP19. The protein concentration was controlled at all steps by measuring A260/A280. The concentration was determined according to the formula c(mg/ml)=(1.55*A280)−(0.76*A260). Finally a 150 ml sample was obtained with a protein concentration 30.8 mg/ml, indicating that the productivity of AFP19 was >1 g/kg fermentation broth. The final preparation was freeze dried and stored at −20° C. until use.

Example 3

Expression and Fermentation of the AFP19 Gene in *Aspergillus oryzae*

*Aspergillus oryzae* strain CBS205.89 (deposited at the Centraalbureau voor Schimmelcultures, Utrecht, the Netherlands and publically available) was used as host and circular vectors pGBTOPAFP-19 vector and pGBAAS-4, described in Example 1, were used in a co-transformation protocol. Transformation was performed as described in WO 98/46772 and WO 99/32617, and selection was on acetamide containing media with 20 mM cesium chloride added. Colonies were purified according to standard procedures. Strains containing the AFP19 gene were selected via PCR with primers specific for the AFP19 gene to verify presence of the pGBTOPAFP-19 expression cassette. A single transformant was selected, named AFPao-7, and further replica-plated to obtain a single strain inoculum. As control a strain of *Aspergillus oryzae* was transformed with plasmid pGB-TOP-16 instead of pGBTOAFP-19, and a single strain inocumum was obtained by replica plating. Fresh *A. oryzae* AFPao-7 spores were prepared and cultured as described in example 2. Cultivation was performed for 72 hours at 30° C. and 170 rpm in shake flask. Supernatant was harvested by centrifugation and stored at −20° C. until further analysis.

The concentration of AFP19 protein produced by *Aspergillus oryzae* AFPao-7 was determined using SDS-PAGE analysis of the supernatant and comparison with a serial dilution of the relatively pure AFP19 from *Aspergillus niger* from Example 2. Cultivation supernatant of the control strain lacking the AFP19 gene was analysed in parallel on the same gel. After staining the gel with Coomassie Brilliant Blue, the staining was quantified and compared to the serial dilution of AFP19 from *A. niger*. The amount of AFP19 produced by *Aspergillus oryzae* was estimated to be 0.4 g/l, clearly more than the 61.2 mg/l of LeIBP produced in shake flask in *Pichia pastoris* (Park et al. 2012, supra). This amount was confirmed by measuring the total protein concentration in the supernatant using Bradford protein stain after deducing the staining intensity of the supernatant of the control strain.

Example 4

Analysis of AFP19 from *Aspergillus niger*

AFP19 as isolated in Example 2 from *Aspergillus niger* was further characterized using LC-MS/MS. For this 1 mg AFP19 protein as isolated in Example 2 was diluted until 100 μg/ml in 100 mM NH4HCO3. For deglycosylation, 100 μl of this solution was heated for 10 min at 90° C. 15 μl PNGase F (Sigma, 1 U/μl) was added and then incubated for 4 hours in a thermomixer at 1000 rpm and 37° C. 1% formic acid was added to the samples before measuring. As a control untreated AFP19 protein was analyzed.

For the LC-MS/MS analysis the samples were analyzed on the Acquity I-class-Synapt G2-S (Waters), with the following parameters: Column: Waters Acquity UPLC BEH300 C4 1.7 μm 300 Å pore size 2.1×50 mm column. Column temperature: 75° C. Injection volume: 5 μl. Mobile phase A: Formic Acid 0.1% in Water. Mobile phase B: Formic Acid 0.1% in Acetonitrile. A gradient was applied to the column by varying phase A and B in order to separate different forms of the AFP19 protein.

The MS detector settings were: Acquisition mass range was 500-3500 m/z, Scan time 1 sec, Positive ESI, TOF MS Resolution mode, with data correction with Leu-Enk applied on the fly during the run. Data spectral deconvolution, charge state stripping, was performed with a Waters Mass-Lynx MaxEnt1—software tool: Output mass–resolution=1 Da/channel. Damage model: Gaussian (FWHH=0.750 Da; minim intensity ratios=33% left and right). Iterate to converge.

Figure 2:
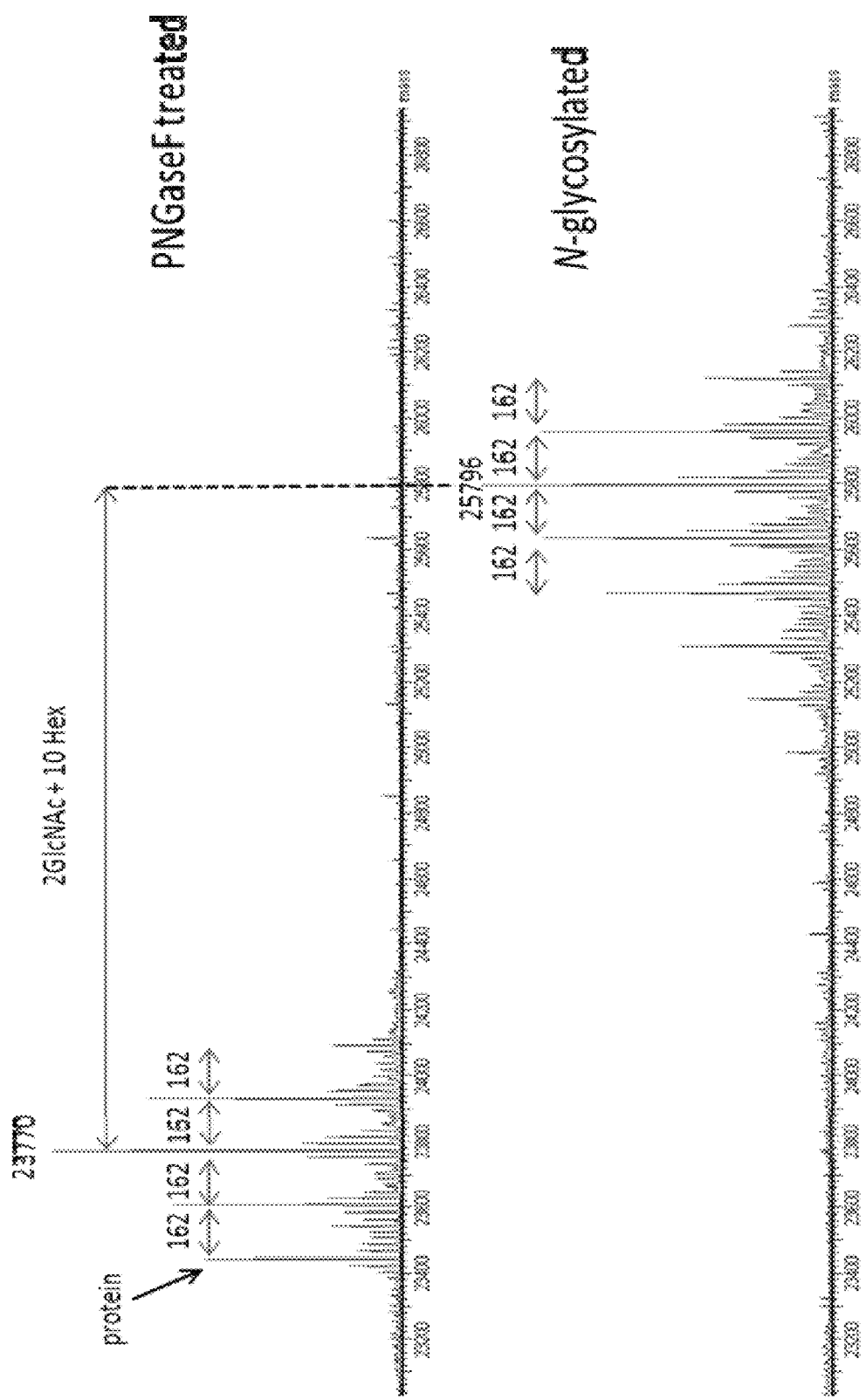
FIG. 2 shows LC MS/MS size determination of AFP19 from *Aspergillus niger*, before and after PNGase F treatment.

The mass of AFP19 was determined before and after enzymatic deglycosylation using this technique and results are depicted in FIG. 2.

Several conclusions can be drawn from these results

The size of the smallest form of AFP19 after PNGase F treatment is 23446 Da. This size is smaller than the calculated molecular weight based on the protein sequence depicted in SEQ ID NO:1 assuming the removal of the pre-sequence after residue 20. This indicates that the AFP19 produced in *A. niger* is missing part of the protein sequence. Since the size does not fit exactly the size of any amino acid deletion, we cannot exclude that other modifications may have occurred during production of AFP19 in *A. niger*. E.g. it is possible that AFP19 contains a pyroglutamate modification at its N-terminus.

AFP19 is heterogenous is size, even after PNGase F treatment. Four peaks with an increment of 162 Da (the size of one hexose unit) are found after PNGase F treatment and the most abundant form being 23770 Da. This indicates that AFP19 produced in *A. niger* contains additional glycosylation, that is not removed by PNGase F. AFP19 may be O-mannosylated up to 4 mannosyl residues per molecule of AFP19, with the most abundant form having 2 mannosyl groups. No O-mannosylation has been detected with the different forms of LeIBP studied in the prior art (Lee et al, 2012, Journal of Biological Chemistry 287, 11460-11468; Lee et al, 2013 supra)

The size difference between the most abundant N-glycosylated form and most abundant deglycosylated form is 2026 Da, indicating that the main N-glycosylated form contains 2 N-acetylglucosamine (GlcNac) and 10 hexose (Hex) units, besides the 2 O-mannoses. The minimum size difference between N-glycosylated AFP19 and PNGase F treated AFP19 is 892 Da, representative for 2 GlcNac and 3 Hex units. This result indicates that all AFP19 forms produced in *A. niger* are differently N-glycosylated (and O-mannosylated) than LeIBP produced in *P. pastoris* which was shown to contain only 2 GlcNac and 2 Hex (Bma and Man) units (Lee et al, 2012).

Using this method it became apparent that the molecular weight of the most abundant form of AFP19 produced in *Aspergillus niger* is 25796 Da. This size is different from the size measured by MALDI-TOF for both the native LeIBP and both non-glycosylated and N-glycosylated forms produced in *E. coli* or *P. pastoris* (Lee et al., 2013).

These results indicate that AFP19 is clearly different from the different forms of LeIBP studied in the prior art.

Example 5

Analysis of AFP19 from *Aspergillus niger* and *Aspergillus oryzae*

AFP19 as isolated in Example 2 (*Aspergillus niger*) and Example 3 (*Aspergillus oryzae*) were further characterized using LC-MS/MS. For this 1 mg AFP19 protein was diluted until 100 µg/ml in 100 mM NH4HCO3. 100 µl of this solution was heated for 10 min at 90° C. AFP19 was analyzed as such, after deglycosylation with PNGase F, after digestion with LysC and after digestion with AspN. For deglycosylation, 15 µl PNGase F (Sigma, 1 U/µl) was added and then incubated for 16 hours in a thermomixer at 1000 rpm and 37° C. 1% formic acid was added to the samples before measuring. As a control untreated AFP19 protein was analyzed.

For the LC-MS/MS analysis the samples were analyzed on the Acquity I-class—Synapt G2-S (Waters), with the following parameters: Column: Acquity UPLC BEH300 C4 1.7 µm 300 Å pore size 2.1×50 mm column (Waters). Column temperature: 75° C. Injection volume: 1 µl. Mobile phase A: Formic Acid 0.1% in Water. Mobile phase B: Formic Acid 0.1% in Acetonitrile. A gradient was applied to the column by varying phase A and B in order to separate different forms of the AFP19 protein.

The MS detector settings were: Acquisition mass range was 500-3500 m/z, Scan time 1 sec, Positive ESI, TOF MS Resolution mode, with data correction with Leu-Enk applied on the fly during the run. Data spectral deconvolution, charge state stripping, was performed with a Waters Mass-Lynx MaxEnt1—software tool: Output mass—resolution=1 Da/channel. Damage model: Gaussian (FWHH=0.750 Da; minim intensity ratios=33% left and right). Iterate to converge. Data spectral deconvolution for ETD, was performed with MassLynx MaxEnt3—software tool for max of 7 charges: no. of ensemble members: 2 and iteration per ensemble member: 50.

For digestion of AFP 19, Lys C and Asp N were used in parallel. 20 µl (2 µg) Lys C or Asp N was added to 100 µl (100 µg) and 400 µl (100 µg) AFP19, respectively. Digestion was performed by incubation at 37° C. overnight. Samples were diluted twice in MilliQ water and samples were acidified to 1% formic acid prior to LC-MS/MS analysis. LC-MS/MS analysis of the digested AFP19 samples were performed on the Ultimate RS 3000 Orbitrap Fusion (Thermo Fisher) with the following parameters: Column: Zorbax XDB-C18 1.8 µm 2.1×50 mm; narrow-bore guard column 2.1×12.5 mm 5-micron, Phoroshell 300SB-C3 (Agilent). Column temperature: 50° C. Injection volume: 25 µl. Mobile phase A: Formic Acid 0.1% in Water. Mobile phase B: Formic Acid 0.1% in Acetonitrile. A gradient was applied to the column by varying phase A and B.

The data were searched against the AFP19 sequence (FDR 0.1%). Database searching was performed on the Proteome Discoverer 1.4.1.14.

Figure 3:
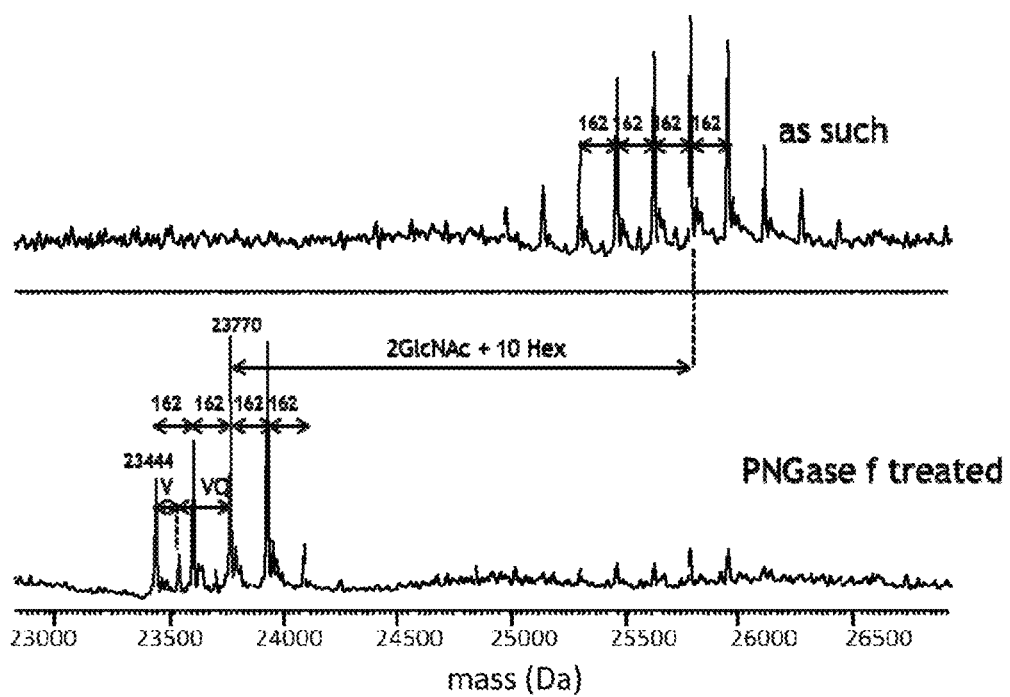
FIG. 3 shows the detected masses of AFP forms before and after deglycosylation with PNGase f. C-terminus truncated form of pyroglutamated AFP are indicated in the Figure with grey rectangles. 162 Da represents the mass of a hexose.

The deconvoluted mass spectra of intact AFP19 before and after PNGase F deglycosylation are shown In FIG. 3.

These data showed that the AFP19 expressed in *A. niger* has a pyroglutamate at the amino-terminus. This observation was confirmed by Electron Transfer Dissociation (ETD) on the intact enzyme as well as by identification of the N-terminal peptide after LysC digestion of AFP19. Pyroglutamate can play an important role in enzyme stability and has not been described in previous literature on LeIBP (Lee et al, 2012 supra; Lee et al, 2013 supra).

Comparing the LC-MS data on intact AFP19 before and after deglycosylation showed that the main N-glycosylated form contains 2 N-acetylglucosamine (GlcNAc) and 10 hexose (Hex) units as indicated in FIG. 3. The deglycosylated AFP19 showed mass increments of 162 Da, indicating that the enzyme is also O-mannosylated, next to the N-glycosylation. These findings were confirmed on the AspN digest of AFP19, where O-mannosylation was identified on position S80 and T84 in SEQ_ID NO:1. The most abundant form of AFP19 contains one O-mannosyl group. Besides the amino-terminal pyroglutamate, also O-mannosylation may have a positive effect on enzyme stability. Again, these findings have not been described in previous literature on AFP (Lee et al, 2012 supra; Lee et al, 2013 supra). The observations on both the N-glycosylation and the O-mannosylation showed that the glycosylation pattern of AFP19 described here is distinctly different from the native LeIBP or LeIBP produced in *Pichia pastoris* (Lee et al, 2012 supra).

The LC-MS analysis on intact AFP19 before and after deglycosylation further showed that the enzyme expressed in *A. niger* has a truncation at the C-terminus. The observed masses 23444 Da, 23543 Da and 23770 Da, respectively correspond to AFP19 with pyroglutamate at the N-terminus and lacking VVQKRSNARQWL (SEQ ID NO:4), VQKRSNARQWL (SEQ ID NO:5), and KRSNARQWL (SEQ ID NO:6), at the C-terminus.

The above mentioned experiments were also performed on AFP19 expressed in *Aspergillus oryzae* (sample as produced in Example 3). These data confirmed that expression in *A. oryzae* also results in AFP with pyroglutamate at the N-terminus and the N-glycosylation and O-mannosylation patterns were highly similar to that of AFP19 expressed in *A. niger*. Furthermore neither the mass of native LeIBP (25565 Da), from *E. coli*, nor the mass of glycosylated LeIBP (26198 Da) and non-glycosylated (25150 Da) LeIBP from *P. pastoris* reported before (Lee et al., 2013) were detected in our samples.

Example 6

Ice Re-Crystallization Inhibition with AFP from *Aspergillus niger*

The RI endpoint for type III AFP from ocean pout in 30% sucrose was reported to be >700 nM by two different authors (Smallwood et al., 1999, supra; Tomczak et al., 2003, supra). The RI endpoint is the concentration below which RI activity was no longer detected. Since the RI endpoint is an important parameter for determination of the effectiveness of an ISP in the inhibition of ice-recrystallization, we decided to determine the RI endpoint in 30% sucrose for AFP19 using the modified splat assay essentially as described in Tomczak et al., 2003, supra.

A 30% (w/v) sucrose solution was supplemented with 100 mg/l whey protein isolate (WPI—Mullins whey) as control or 4000, 80 and 20 nM of AFP19 from *Aspergillus niger* prepared according to Example 2. For this experiment 23 mg AFP19 was dissolved in 4.6 ml distilled water and from this solution 50-, 2500-, 10000-fold dilutions were made in the 30% sucrose solution.

10 microliter of these solutions was used for the preparation of the microscopic samples and mounted onto a Zeiss Axiophot microscope equipped with a cooling stage. Imaging was performed using a CCD camera equipped on the microscope. Magnification was 6.3 fold and crystal formation in the samples was followed in time.

First the samples were cooled at a rate of 90° C. per second until −60° C. After this the samples were warmed at the same rate until −6° C. and ice crystal formation was followed in time. After 0, 3, 9 and 60 minutes pictures were taken and used for the measurement of the average ice crystal size using Linksys32 software (Linkam Scientific Instruments). Results of this experiment are shown in Table 1 which shows clearly that AFP19 inhibits ice recrystallization. No growth of ice crystals in time could be detected even when the concentration of AFP19 is only 20 nM. The control sample with WPI shows however a clear increase in the crystal size in time.

These results show that the RI endpoint in 30% sucrose for AFP19 is clearly lower than 20 nM. This value is much lower than the RI endpoint reported for type III AFP from ocean pout (Tomczak et al, 2003 supra: 780 nM). Thus, AFP19 is much more effective than the current industry standard type III HPLC12 AFP in inhibition of ice-recrystallization.

TABLE 1

Minimum and maximum size [micrometer] of ice crystals in time

|  | T = 3 min | T = 9 min | T = 60 min |
|---|---|---|---|
| control | 8-10 | 15-93 | 24-185 |
| 4000 nM AFP19 | 5-11 | 6-9 | 4-13 |
| 80 nM AFP19 | 8-25 | 9-29 | 10-30 |
| 20 nM AFP19 | 8-27 | 7-29 | 7-33 |

Example 7

Sorbet Ice Produced with AFP19 from *Aspergillus niger*

Sorbet was produced by mixing 100 gram sugar, 400 ml water and 60 gram of lemon juice. Control protein (WPI) or AFP19 from *Aspergillus niger* prepared according to Example 2 was added at 40 or 400 nM. Sorbet was produced by processing 560 g batches of this mixture in a Gel5 table-top ice making machine (CRM/Telme) at standard settings. After production the sorbet was removed from the machine and instantly frozen and stored in 100 gram portions at −30° C. for the amount of days required before analysis (maximum 4 weeks).

Example 8

Sensory Analysis of Sorbets Produced with AFP19 from *Aspergillus niger*

Portions of sorbets as described in Example 7 were removed from the freezer 15 minutes before assessment and allowed to warm at room temperature. Sensory analysis was performed by a panel consisting of 5 persons and sorbets were assessed for scoopability, color, mouth-feel, flavor and general appearance. All assessors agreed that both sorbets made with AFP19 from *Aspergillus niger* prepared according to Example 2 were significantly different from the control sorbets. AFP19 sorbets were found more white in appearance, more firm at scooping, and having a smoother mouth-feel compared to control sorbets. No significant differences were found in flavor perception.

Example 9

Melting Behavior of Sorbets Produced with AFP19 Form *Aspergillus niger*

Figure 4:
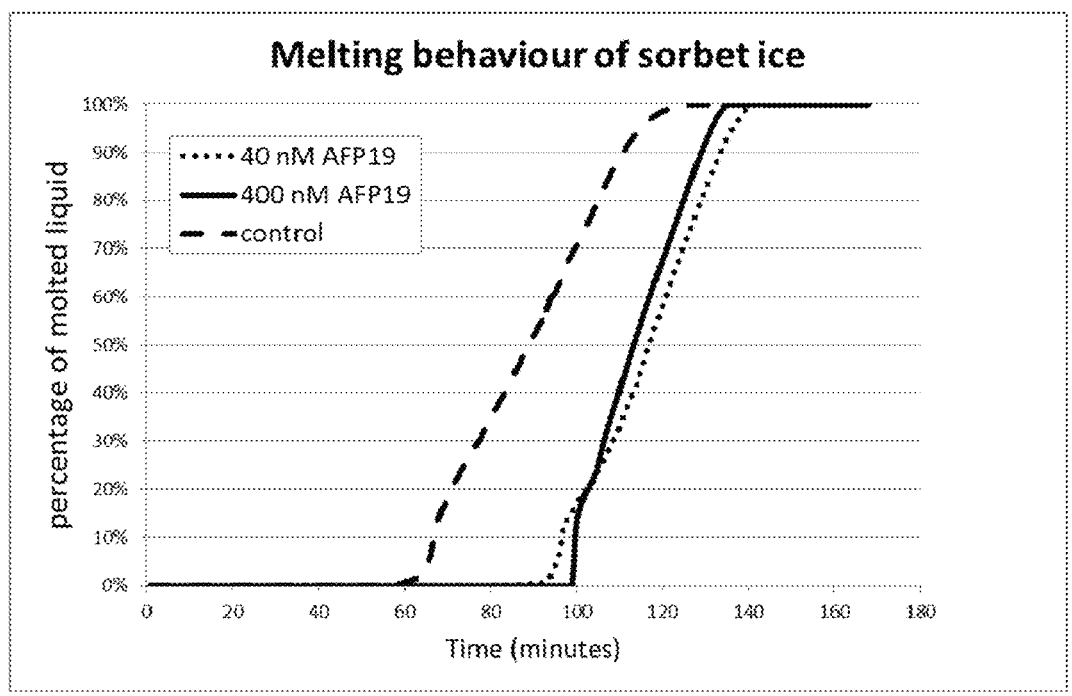
FIG. 4 shows the melting behavior of sorbet ice produced with AFP19 from *Aspergillus niger*.

Sorbets produced in Example 6 were allowed to melt at a controlled temperature of 25° C. over a 1 mm mesh sieve. The melt was collected and the weight was measured continuously on a balance. Results of this experiment can be seen in FIG. 4. A clear difference in melting behavior was seen between the sorbets made with AFP19 from *Aspergillus niger* prepared according to Example 2 and the control sorbets. Sorbets made with AFP19 remain frozen for a longer period of time. This effect was observed both at 40 and 400 nM AFP19.

Example 10

Ice Cream Produced with AFP19 from *Aspergillus niger*

Ice cream was produced by mixing:

| Dairy cream | 286 g |
|---|---|
| Skim milk powder | 206 g |
| Sugar | 240 g |
| Glucose syrup | 80 g |

Make up a total of 2 kg using hot water.

The mix was pasteurized by heating in a water bath set at 95° C. for 30 min. The mix was cooled and ripened for 16 h at 4° C. The mix was homogenized and filtered before separation in 3 portions of 650 g; one control without additions, one portion obtained 40 nM AFP19 from *Aspergillus niger* prepared according to Example 2 and one portion obtained 400 nM AFP19 from *Aspergillus niger* prepared according to Example 2. Ice cream was produced by processing the batches in a Gel5 table-top ice making machine (CRM/Telme) at standard settings. After production the ice cream was removed from the machine and instantly frozen and stored in 100 gram portions at −30° C. for the amount of days required before analysis (maximum 4 weeks).

Sensory analysis of the ice cream produced with AFP19 resulted in the same conclusions as described for the production of sorbet ice in Example 8: both ice creams made with AFP19 were more firm upon scooping and had a smoother mouth-feel compared to the control ice cream Example 11

Melting Behavior of Ice Cream Produced with AFP19 from *Aspergillus niger*

Figure 5:
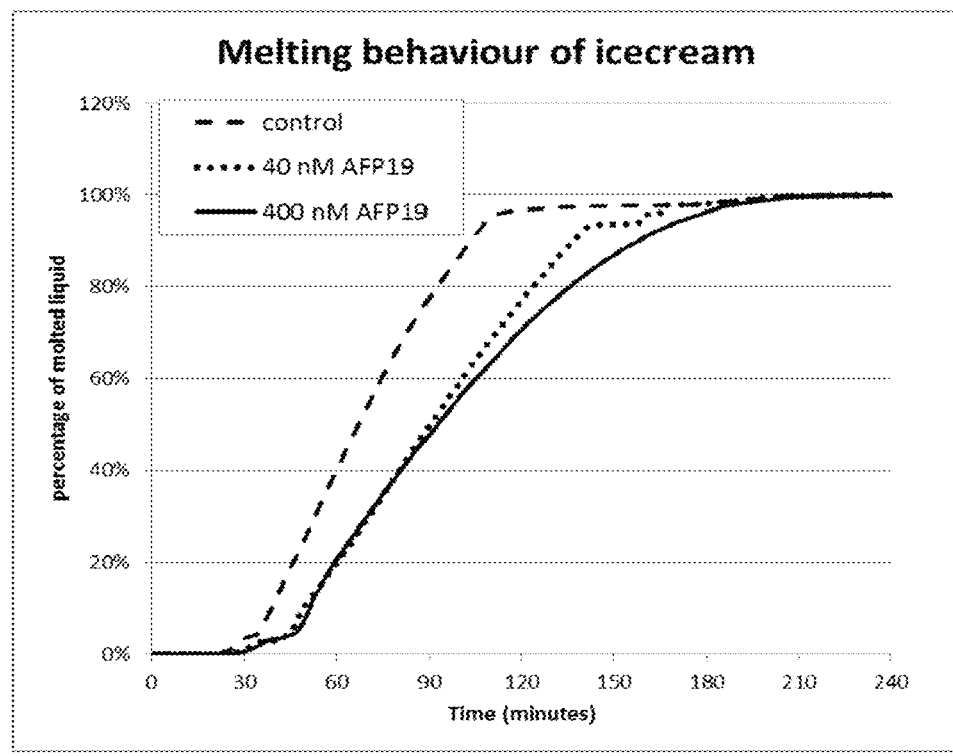
FIG. 5 shows the melting behavior of ice cream produced with AFP19 from *Aspergillus niger*.

Ice creams produced in Example 10 were allowed to melt at a controlled temperature of 25° C. over a 1 mm mesh sieve. The melt was collected and the weight was measured continuously on a balance. Results of this experiment can be seen in FIG. 5. A clear difference in melting behavior was seen between the ice cream made with AFP19 from *Aspergillus niger* prepared according to Example 2 and the control ice cream. Ice cream made with AFP19 remain frozen for a longer period of time. This affect was observed both at 40 and 400 nM AFP19, which much lower than the dosage recommended in ice cream (7 µM) for type III HPLC12 AFP from ocean pout (Lewis, 2006 supra).

The invention claimed is:

1. An ice structuring protein (ISP) made in a filamentous fungal host cell of the genus *Aspergillus*, the ISP comprising:
   an amino add sequence at least 80% identical to the sequence set out in SEQ ID NO: 1 or comprising an amino add sequence at least 80% identical to the sequence set out in amino adds 21 to 261 of SEQ ID NO: 1, and,
   a pyroglutamate present at the N-terminus.

2. The ISP according to claim 1, wherein the ISP comprises an amino sequence at least 85% identical to the sequence set out in SEQ ID NO: 1 or comprises an amino acid sequence at least 85% identical to the sequence set out in amino acids 21 to 261 of SEQ ID NO: 1.

3. The ISP according to claim 1, wherein the amino acid sequence of SEQ ID NO: 1 is encoded by a nucleic acid from an arctic yeast of the genus *Leucosporidium*.

4. A filamentous fungal host cell of the genus *Aspergillus* which comprises the ISP according to claim 1.

5. The filamentous fungal host cell according to claim 4, wherein the filamentous fungal host cell is selected from the group consisting of *Aspergillus niger* and *Aspergillus oryzae*.

6. A method for the production of the ice structuring protein (ISP) of claim 1, which method comprises:
   providing the filamentous fungal host cell of the genus *Aspergillus* of claim 1, wherein the filamentous fungal host cell contains a nucleic acid sequence encoding the amino acid sequence at least 80% identical to the sequence set out in SEQ ID NO: 1 or the amino acid sequence at least 80% identical to the sequence set out in amino acids 21 to 261 of SEQ ID NO: 1;
   cultivating the filamentous fungal host cell under conditions suitable for production of the ice structuring protein; and, optionally
   recovering the ice structuring protein.

7. The method according to claim 6, wherein the ISP comprises an amino sequence at least 85% identical to the sequence set out in SEQ ID NO:1 or comprises an amino acid sequence at least 85% identical to the sequence set out in amino acids 21 to 261 of SEQ ID NO:1.

8. The method according to claim 6, wherein the ISP is secreted from the host cell.

9. The method according to claim 6, wherein the ISP is produced at an amount of at least 1 g/l.

10. An ice structuring protein made in a filamentous fungal host cell of the genus *Aspergillus*, comprising an amino add sequence at least 80% identical to the sequence set out in SEQ ID NO: 1, an amino acid sequence at least 80% identical to the sequence set out in amino acids 21 to 261 of SEQ ID NO: 1 an amino acid sequence at least 80% identical to the sequence set out in amino acids 21 to 249 of SEQ ID NO: 1, or to amino acids 21-250 of SEQ ID NO: 1, or to amino acids 21-251 of SEQ ID NO: 1, wherein the protein has a pyroglutamate present at the N-terminus; and
   (a) at least one amino acid is O-mannosylated; or
   (b) the protein has a glycosylation pattern other than 2GlcNac and 2 hexose units.

11. A food composition comprising the ice structuring protein according to claim 10.

12. A method for the preparation of a food product, which method comprises combining the ice structuring protein according to claim 10 with one or more food ingredients.

13. The ice structuring protein according to claim 10 in a food composition.

14. The food composition according to claim 11, wherein the food composition is frozen confectionary product.

15. The food composition according to claim 11, wherein the food composition is an ice cream or a sorbet.

16. The ISP according to claim 1, wherein the ISP comprises an amino sequence at least 90% identical to the sequence set out in SEQ ID NO: 1 or comprises an amino acid sequence at least 90% identical to the sequence set out in amino acids 21 to 261 of SEQ ID NO: 1.

17. The ISP according to claim 1, wherein the ISP comprises an amino sequence at least 95% identical to the sequence set out in SEQ ID NO: 1 or comprises an amino acid sequence at least 95% identical to the sequence set out in amino acids 21 to 261 of SEQ ID NO: 1.

18. The method according to claim 6, wherein the filamentous fungal host cell is selected from the group consisting of *Aspergillus niger* and *Aspergillus oryzae*.

19. A filamentous fungal host cell which comprises a nucleic acid construct or
   an expression vector comprising a nucleic acid construct, wherein the filamentous fungal host cell is of the genus *Aspergillus*, and wherein said nucleic acid construct comprises:
      a nucleic acid sequence encoding an ice structuring protein (ISP) comprising the sequence set out in SEQ ID NO: 1 or a sequence at least 80% identical thereto or comprising the sequence set out in amino acids 21 to 261 of SEQ ID NO: 1 or a sequence at least 80% identical thereto; and, linked operably thereto, and
   control sequences permitting expression of the nucleic acid sequence in the filamentous fungal host cell.

\* \* \* \* \*

SEQUENCE LISTING

<160> NUMBER OF SEQ ID NOS: 3

<210> SEQ ID NO 1
<211> LENGTH: 261
<212> TYPE: PRT
<213> ORGANISM: Leucosporidium

<400> SEQUENCE: 1

| Met | Ser | Leu | Leu | Ser | Ile | Ile | Thr | Ile | Gly | Leu | Ala | Gly | Leu | Gly | Gly |
|---|---|---|---|---|---|---|---|---|---|---|---|---|---|---|---|
| 1 | | | | 5 | | | | | 10 | | | | | 15 | |

| Leu | Val | Asn | Gly | Gln | Arg | Asp | Leu | Ser | Val | Glu | Leu | Gly | Val | Ala | Ser |
|---|---|---|---|---|---|---|---|---|---|---|---|---|---|---|---|
| | | | 20 | | | | | 25 | | | | | 30 | | |

| Asn | Phe | Ala | Ile | Leu | Ala | Lys | Ala | Gly | Ile | Ser | Ser | Val | Pro | Asp | Ser |
|---|---|---|---|---|---|---|---|---|---|---|---|---|---|---|---|
| | | | 35 | | | | | 40 | | | | | 45 | | |

| Ala | Ile | Leu | Gly | Asp | Ile | Gly | Val | Ser | Pro | Ala | Ala | Ala | Thr | Tyr | Ile |
|---|---|---|---|---|---|---|---|---|---|---|---|---|---|---|---|
| | 50 | | | | | 55 | | | | | 60 | | | | |

| Thr | Gly | Phe | Gly | Leu | Thr | Gln | Asp | Ser | Ser | Thr | Thr | Tyr | Ala | Thr | Ser |
|---|---|---|---|---|---|---|---|---|---|---|---|---|---|---|---|
| 65 | | | | | 70 | | | | | 75 | | | | | 80 |

| Pro | Gln | Val | Thr | Gly | Leu | Ile | Tyr | Ala | Ala | Asp | Tyr | Ser | Thr | Pro | Thr |
|---|---|---|---|---|---|---|---|---|---|---|---|---|---|---|---|
| | | | | 85 | | | | | 90 | | | | | 95 | |

| Pro | Asn | Tyr | Leu | Ala | Ala | Ala | Val | Ala | Asn | Ala | Glu | Thr | Ala | Tyr | Asn |
|---|---|---|---|---|---|---|---|---|---|---|---|---|---|---|---|
| | | | 100 | | | | | 105 | | | | | 110 | | |

| Gln | Ala | Ala | Gly | Phe | Val | Asp | Pro | Asp | Phe | Leu | Glu | Leu | Gly | Ala | Gly |
|---|---|---|---|---|---|---|---|---|---|---|---|---|---|---|---|
| | | | 115 | | | | | 120 | | | | | 125 | | |

| Glu | Leu | Arg | Asp | Gln | Thr | Leu | Val | Pro | Gly | Leu | Tyr | Lys | Trp | Thr | Ser |
|---|---|---|---|---|---|---|---|---|---|---|---|---|---|---|---|
| | 130 | | | | | 135 | | | | | 140 | | | | |

| Ser | Val | Ser | Val | Pro | Thr | Asp | Leu | Thr | Phe | Glu | Gly | Asn | Gly | Asp | Ala |
|---|---|---|---|---|---|---|---|---|---|---|---|---|---|---|---|
| 145 | | | | | 150 | | | | | 155 | | | | | 160 |

| Thr | Trp | Val | Phe | Gln | Ile | Ala | Gly | Gly | Leu | Ser | Leu | Ala | Asp | Gly | Val |
|---|---|---|---|---|---|---|---|---|---|---|---|---|---|---|---|
| | | | | 165 | | | | | 170 | | | | | 175 | |

| Ala | Phe | Thr | Leu | Ala | Gly | Gly | Ala | Asn | Ser | Thr | Asn | Ile | Ala | Phe | Gln |
|---|---|---|---|---|---|---|---|---|---|---|---|---|---|---|---|
| | | | 180 | | | | | 185 | | | | | 190 | | |

| Val | Gly | Asp | Asp | Val | Thr | Val | Gly | Lys | Gly | Ala | His | Phe | Glu | Gly | Val |
|---|---|---|---|---|---|---|---|---|---|---|---|---|---|---|---|
| | | | 195 | | | | | 200 | | | | | 205 | | |

| Leu | Leu | Ala | Lys | Arg | Phe | Val | Thr | Leu | Gln | Thr | Gly | Ser | Ser | Leu | Asn |
|---|---|---|---|---|---|---|---|---|---|---|---|---|---|---|---|
| | 210 | | | | | 215 | | | | | 220 | | | | |

| Gly | Arg | Val | Leu | Ser | Gln | Thr | Glu | Val | Ala | Leu | Gln | Lys | Ala | Thr | Val |
|---|---|---|---|---|---|---|---|---|---|---|---|---|---|---|---|
| 225 | | | | | 230 | | | | | 235 | | | | | 240 |

| Asn | Ser | Pro | Phe | Val | Pro | Ala | Pro | Glu | Val | Val | Gln | Lys | Arg | Ser | Asn |
|---|---|---|---|---|---|---|---|---|---|---|---|---|---|---|---|
| | | | | 245 | | | | | 250 | | | | | 255 | |

| Ala | Arg | Gln | Trp | Leu |
|---|---|---|---|---|
| | | | | 260 |

<210> SEQ ID NO 2
<211> LENGTH: 786
<212> TYPE: DNA
<213> ORGANISM: Leucosporidium

<400> SEQUENCE: 2

| atgagccttc | tctccatcat | caccattggt | cttgctggct | tgggtggtct | ggtcaacggc | 60 |
|---|---|---|---|---|---|---|
| cagcgtgacc | tctccgttga | gcttggagtt | gcctccaact | tcgccatcct | ggccaaggcc | 120 |
| ggtatctcct | ccgtgcctga | ctctgccatc | ctcggtgaca | tcggtgtctc | tcctgctgct | 180 |
| gccacctaca | tcaccggctt | cggtctcacc | caggacagca | gcaccaccta | cgccacctcg | 240 |
| ccccaggtca | ctggtctcat | ctacgctgcc | gactacagca | ctcccacccc | caactacctg | 300 |

```
gctgctgctg ttgccaacgc cgagactgcc tacaaccagg ctgctggctt cgtcgacccc    360
gacttcctgg agcttggtgc tggtgagctg cgtgaccaga ctctggtgcc tggtctctac    420
aagtggacct cctccgtctc cgttcctact gacttgacct tcgagggcaa cggcgatgcc    480
acctgggtgt tccagattgc tggtggtctc tccctcgccg atggtgttgc tttcaccctg    540
gctggtggtg ccaactcgac caacattgct ttccaggtcg gcgatgatgt cactgtcggc    600
aagggtgctc acttcgaggg tgtcctcctt gccaagcgct tcgtcaccct ccagactggc    660
tcttctctga acggccgtgt cctgagccag accgaggttg ctctccagaa ggccaccgtc    720
aactctccct tcgtccccgc tcccgaggtt gtgcagaagc gctccaacgc ccgccagtgg    780
ctataa                                                               786

<210> SEQ ID NO 3
<211> LENGTH: 1059
<212> TYPE: DNA
<213> ORGANISM: Artificial sequence
<220> FEATURE:
<223> OTHER INFORMATION: A DNA fragment (comprising the expression
      cassette as in SEQ ID NO: 3) containing a.o. part of the
      glucoamylase promoter and the ISP encoding gene

<400> SEQUENCE: 3
agagcttgaa gtggcgagat gtctctgcag gaattcaagc tagatgctaa gcgatattgc     60
atggcaatat gtgttgatgc atgtgcttct tccttcagct tcccctcgtg cagatgaggt    120
ttggctataa attgaagtgg ttggtcgggg ttccgtgagg ggctgaagtg cttcctccct    180
tttagacgca actgagagcc tgagcttcat ccccagcatc attacaccgt caaaatgagc    240
cttctctcca tcatcaccat tggtcttgct ggcttgggtg gtctggtcaa cggccagcgt    300
gacctctccg ttgagcttgg agttgcctcc aacttcgcca tcctggccaa ggccggtatc    360
tcctccgtgc ctgactctgc catcctcggt gacatcggtg tctctcctgc tgctgccacc    420
tacatcaccg gcttcggtct cacccaggac agcagcacca cctacgccac ctcgccccag    480
gtcactggtc tcatctacgc tgccgactac agcactccca ccccaactac cctggctgct    540
gctgttgcca acgccgagac tgcctacaac caggctgctg gcttcgtcga ccccgacttc    600
ctggagcttg gtgctggtga gctgcgtgac cagactctgg tgcctggtct ctacaagtgg    660
acctcctccg tctccgttcc tactgacttg accttcgagg gcaacggcga tgccacctgg    720
gtgttccaga ttgctggtgg tctctcccte gccgatggtg ttgctttcac cctggctggt    780
ggtgccaact cgaccaacat tgctttccag gtcggcgatg atgtcactgt cggcaagggt    840
gctcacttcg agggtgtcct ccttgccaag cgcttcgtca ccctccagac tggctcttct    900
ctgaacggcc gtgtcctgag ccagaccgag gttgctctcc agaaggccac cgtcaactct    960
cccttcgtcc ccgctcccga ggttgtgcag aagcgctcca acgcccgcca gtggctataa   1020
attaattaac aatcaatcca tttcgctata gttaaagga                          1059
```